(12) United States Patent
Palenchar et al.

(10) Patent No.: US 7,739,053 B2
(45) Date of Patent: Jun. 15, 2010

(54) SYSTEM AND PROCESS OF DETERMINING A BIOLOGICAL PATHWAY BASED ON A TREATMENT OF A BIOLOGICAL SPECIMEN

(75) Inventors: Peter Palenchar, New York, NY (US); Dennis Shasha, New York, NY (US); Michael Chou, Boston, MA (US); Marc Rejali, London (GB); Yair Dorsett, New York, NY (US); Andrei Kouranov, Philadelphia, PA (US); Gloria Coruzzi, New York, NY (US)

(73) Assignee: New York University, New York, NY (US)

( * ) Notice: Subject to any disclaimer, the term of this patent is extended or adjusted under 35 U.S.C. 154(b) by 746 days.

(21) Appl. No.: 11/035,546

(22) Filed: Jan. 14, 2005

(65) Prior Publication Data

US 2005/0260615 A1    Nov. 24, 2005

Related U.S. Application Data

(60) Provisional application No. 60/536,654, filed on Jan. 15, 2004.

(51) Int. Cl.
*G01N 33/48* (2006.01)
(52) U.S. Cl. ...................................................... 702/19
(58) Field of Classification Search ................... 702/19
See application file for complete search history.

(56) References Cited

U.S. PATENT DOCUMENTS

| 6,023,659 | A | 2/2000 | Seilhamer et al. | |
| 6,470,277 | B1 | 10/2002 | Chin et al. | |
| 2004/0024543 | A1* | 2/2004 | Zhang et al. | 702/32 |

OTHER PUBLICATIONS

Hakamada et al. "A Preprocessing Method for Inferring Genetic Interaction from Gene Expression Data Using Boolean Algorithm," Journal of Bioscience and Bioengineering (Jun. 2004) vol. 98, No. 6, pp. 457-463.*

Gail Dutton, "Gene Expression Data Mining" The Scientist, Oct. 14, 2002, pp. 50-53.
Peter D. Karp et al., "The Metacyc Database" Nucleic Acids Research 2002 30(1):59-61, by Jan. 25, 2002, pp. 7.
The Plant Cell, "Plant Metabolomics: The Missing Link in Functional Genomics Strategies" American Society of Plant Biologists, vol. 14, Jul. 2002, pp. 1437-1440.
CuraGen Corporation, "Path Calling®" Rapidly Identifies Novel Protein Pathways and Interactions using Industrialized Proteomica Technology, pp. 1-3.
Peter Karp et al., "The Pathway Tools Software" Bioinformatics, by Jan. 24, 2004, pp. S1-S8.
Peter Karp et al., "Pathway Databases: A Case Study in Computational Symbolic Theories" Science, vol. 293, Sep. 14, 2001, pp. 2040-2044.
"Microarray Analysis", BioMedNet Online Magazine, Oct. 10, 2002, pp. 1-19.
BayGenomics, "Expression Profiling and Analysis", Oct. 15, 2002, pp. 1-2.
"SMD Microarray Links: Software & Tools", Microarray Resources, Oct. 15, 2002, pp. 1-2.

* cited by examiner

*Primary Examiner*—Jerry Lin
(74) *Attorney, Agent, or Firm*—Dorsey & Whitney LLP

(57) ABSTRACT

Provided herein is a system and method for analyzing microarray data (transcriptome profiles), metabolite data (metabolome profiles), protein level data (proteome profiles), or any combination thereof to determine the biochemical pathways affected by a treatment. The system and method can be used to generate biochemical pathway information for any organism for which metabolic profile data can be obtained. The system and method may allow users to query the pathways generated and to filter the results of queries based on the -omic profile data, pathways involving molecules of interest, notions of biochemical importance, milestone molecules, and other factors. The system and method may also be suitable for discovery of regulatory sequences in genes. In an exemplary use, the system and method can be utilized to identify three genes involved in "de novo" ammonia "biosynthesis" that are induced by light, and was able to identify a putative cis-element, GWTTGTGG, that is likely involved in the regulation of those genes.

17 Claims, 11 Drawing Sheets

| Pathway 1: L-glutamine to L-glutamate |||||||
| Step 1: L-glutamine (DM; -87) to L-glutamate (ICM; -17) |||||||
| Reaction ID | Enzyme Name | NCBI Gene Name | Gene Value | Gene Regulation | Protein Value | Protein Level |
| --- | --- | --- | --- | --- | --- | --- |
| 1.4.1.13 | glutamate synthase [NADPH] | At5g53460 | -3.4 | DG | -3.7 | DP |
| 1.4.7.1 | glutamate synthase [ferredoxin] | At2g41220 | -2.7 | ICG | -1.9 | ICP |
| 1.4.7.1 | glutamate synthase [ferredoxin] | At5g04104 | -1.9 | DG | -1.9 | ICP |
| | | | | | | |
| Pathway 2: isocitrate to L-glutamate |||||||
| Step 1: isocitrate (ICM; -15.8) to 2-ketoglutarate (IM; 37) |||||||
| Reaction ID | Enzyme Name | NCBI Gene Name | Gene Value | Gene Regulation | Protein Value | Protein Level |
| 1.1.1.42 | isocitrate dehydrogenase [NADP] | At1g65930 | -1.3 | NCG | 4.5 | IP |
| 1.1.1.42 | isocitrate dehydrogenase [NADP] | At5g14590 | 1.4 | ICG | 4.5 | IP |
| 1.1.1.42 | isocitrate dehydrogenase [NADP] | At1g54390 | 1.1 | NCG | 4.5 | IP |
| 1.1.1.41 | isocitrate dehydrogenase [NAD] | At2g17130 | 3.4 | DG | 7.8 | IP |
| 1.1.1.41 | isocitrate dehydrogenase [NAD] | At3g09805 | 1.9 | DG | 7.8 | IP |
| 1.1.1.41 | isocitrate dehydrogenase [NAD] | At4g35650 | 4.2 | DG | 7.8 | IP |
| 1.1.1.41 | isocitrate dehydrogenase [NAD] | At4g35260 | 2.7 | DG | 7.8 | IP |
| | | | | | | |
| Step 2: 2-ketoglutarate (IM; 37) to L-glutamate (ICM; -17) |||||||
| Reaction ID | Enzyme Name | NCBI Gene Name | Gene Value | Gene Regulation | Protein Value | Protein Level |
| 1.4.1.13 | glutamate synthase [NADPH] | At5g53460 | -3.4 | DG | -3.7 | DP |
| 1.4.7.1 | glutamate synthase [ferredoxin] | At2g41220 | -2.7 | ICG | -1.9 | ICP |
| 1.4.7.1 | glutamate synthase [ferredoxin] | At5g04104 | -1.9 | DG | -1.9 | ICP |
| | | | | | | |
| Pathway 3: reduced glutathione to L-glutamate |||||||
| Step 1: reduced gluthathione (DM; -13.2) to L-glutamate ICM; -17) |||||||
| Reaction ID | Enzyme Name | NCBI Gene Name | Gene Value | Gene Regulation | Protein Value | Protein Level |
| 9.2.3.2.2 | gamma-glutamyltranspeptidase | At1g69820 | -1.1 | NCG | 1.8 | NCP |

Figure 8

| Pathway | Protein | Step | Gene Used in Analysis | Average Fold Change |
|---|---|---|---|---|
| pathway 1 (step 1) | ammonia symporter | external $NH_3$ to $NH_3$ | At1g64780 | 4.95 |
| pathway 2 (step 1) | nitrate symporter | external nitrate to nitrate | At3g21670 | 6.5 |
| pathway 2 (step 2) | nitrate reductase | nitrate to nitrite | At1g77760 | 5.55 |
| pathway 2 (step 3) | nitrite reductase | nitrite to ammonia | | |

Figure 9

| Motif Name[1] | Sequence Found by AlignACE | Sequence in Plant Care Database | Function Found in Plant Care | Percentage of Induced Genes With Motif | Transcription Correlation Statistics[2] |
|---|---|---|---|---|---|
| TCA element | AGRAGAA | GAGAAGAATA | involved in salicylic acid response | 15.8% | all copy number disfavor induction |
| LAMP | CNNAAACMA | CCAAAACCA | part of a light response element | 21.8% | high copy favored induction |
| GATA box | ACCAMANNNA | TTACCACAGAAACC | responses element to auxin-free medium | 22% | high copy number favored induction |
| HSE | AAANAAWT | AAAAAATTTC | involved in heat stress response | 19.7% | not statistically significant |
| AAAC motif | CAMWCAA | CAATCAAAACCT | light response element | 18.9% | not statistically significant |
| AAAC motif | ACMAAAA | CAATCAAAACCT | light response element | 21.5% | not statistically significant |
| GT-1 | GWGKTTG | ATGGTGGTTGG | light response element | 20.7% | not statistically significant |
| Motif 1 | ARNGWGAG | Not Found | Not Found | 18.7% | high copy number disfavors induction |
| Motif 3 | CNAAAANNA | not found | not found | 21.3% | not statistically significant |
| Motif 4 | AAANCAAA | not found | not found | 18.7% | not statistically significant |
| Motif 5 | GRGARGG | not found | not found | 17.9% | low copy number disfavors induction |
| Motif 8 | CACAAAM | not found | not found | 21% | not statistically significant |
| Motif 10 | GWGNNGAGNNA | not found | not found | 20.2% | not statistically significant |
| Motif 14 | GWTTGTGG | not found | not found | 21.6% | low copy favors induction[3] |
| Motif 15 | TGTGGTYG | not found | not found | 28.7% | high copy favors induction |

Figure 10

| Motif Name | Number of Consistently Expressed Genes with Motif | Number of Induced Genes with Motif | p-value |
|---|---|---|---|
| Motif 14 | 211 all copy | 61 | 0.0012 |
| Random 1a | 22 high copy genes | 4 | 0.039 |
| Random 1b | 24 high copy genes | 9 | 0.022 |
| Random 1c | 199 high copy genes | 53 | 0.0199 |
| Random 2a | 889 all copy | 206 | 0.0066 |
| Random 3a | 30 high copy genes | 12 | 0.0054 |
| Random 3b | 217 all copy | 55 | 0.025 |

Figure 11

|  | Motif | Motif found by AlignACE |
|---|---|---|
| Motif | 14 | GWT*T*GTGG |
| Motif | 13 | *T*GTGGTYG |
| GT-1 |  | GW<u>G</u>KTTG |
| Motif | 14 | <u>GWTTGTGG</u> |

Figure 12

| Gene | Protein |
|---|---|
| energy/photosynthesis related genes | |
| At4g32260 | H+-transporting ATP synthase chain 9 |
| At3g54890 | chlorophyll a/b-binding protein |
| At3g27690 | chlorophyll A-B binding protein |
| signaling, sensing and regulatory genes | |
| At4g04850 | putative potassium transporter |
| At3g27925 | DegP protease precursor |
| At3g55380 | E2, ubiquitin-conjugating enzyme 14 |
| At2g29120 | ligand-gated ion channel protein |
| At2g03710 | MADS-box protein (AGL3) |
| At2g46430 | putative cyclic nucleotide-regulated ion channel protein |
| At4g23740 | putative receptor kinase |
| At1g60800 | receptor-like kinase |
| At4g27760 | forever young gene |
| amino acid biosynthesis | |
| At2g57890 | glutamate kinase |
| At4g39870 | phosphoglutamate reductase |
| At1g12780 | argininosuccinate synthetase |
| At3g12570 | glutamine synthetase |
| other metabolic genes | |
| At1g32200 | glycerol-3-phosphate acyltransferase |

Figure 13

SYSTEM AND PROCESS OF DETERMINING A BIOLOGICAL PATHWAY BASED ON A TREATMENT OF A BIOLOGICAL SPECIMEN

CROSS REFERENCE TO RELATED APPLICATION

This application relates to U.S. Patent Application Ser. No. 60/536,654, filed Jan. 15, 2004, the entire disclosure is incorporated herein by reference.

FIELD OF THE INVENTION

The present invention relates to methods and systems for generating biological pathways and metabolic relationships from libraries, databases, and instruments that provide data associated with metabolites, enzymes, proteins, transporters and genetic expression.

BACKGROUND INFORMATION

All organisms respond to external stimuli in their environment. Changes in the transcriptional regulation of genes are a key component of these responses. Understanding the response of an organism to external stimuli at the biochemical level is necessary to truly understand the resulting physiological changes. In bacteria, biochemically related genes are frequently found in the same operon, resulting in their co-transcription. In some eukaryotes, it is known that some biochemically related genes are under the control of the same transcription factor, which will result in their cotranscription, as described in Greenberg, M. L. et al., "Genetic regulation of phospholipid biosynthesis in *Saccharomyces cerevisiae*," Microbiological Reviews. 1: 1-7, 1996, and Batzer, M. A. et al., "Alu repeats and human genomic diversity," Nat. Rev. Genet. 3: 370-379, 2002.

In plants, little is known about the co-regulation of genes that encode for enzymes that make up biochemical pathways. However, from what is known, it is reasonable to expect many of the enzymes in a biochemical pathway to have genes that are co-regulated in plants. For example, a recent genomic analysis of nitrate-treated *Arabidopsis* has shown that a set of genes encoding enzymes and cofactors involved in nitrate reduction are induced by nitrate as described in Wang, R. C. et al., "Genomic analysis of a nutrient response in *arabidopsis* reveals diverse expression patterns and novel metabolic and potential regulatory genes induced by nitrate," Plant Cell 12:155-171, 2000.

Therefore, the analysis of microarray expression data in relation to metabolic pathways may be a powerful tool in determining the underlying causes of a physiological response in an organism. This realization led to the development of tools to analyze gene expression with respect to pathways. These tools include AraCyc and the PathDB/ISYS/MaxdViewer system. While these tools are useful, they may be currently limited to the analysis of gene expression data only, which is only an approximation of the in vivo level of the protein. Recent advances in measuring metabolite profiles in plants ensure progress in the field of plant metabolomics, as described in Fiehn, O., "Metabolomics—the link between phenotypes and genotypes," Plant Mol. Biol. 48:155-171, 2002

While the inability to measure the levels of individual proteins in plants in a high-throughput manner currently has limited the growth of the plant proteomics field as described in Kersten, B. et al., "Large-scale plant proteoics," Plant Mol. Biol. 48:133-141, 2002.

there is remains a need in the bioinformatics arts generally, for a tool capable of analyzing each of proteomic, transcriptosomic and metabolomic types of profile data, either individually or collectively.

SUMMARY OF THE INVENTION

The present invention relates to such a tool exemplified by the methods implemented in a system herein designated as "PathExplore", which is the first system operable to analyze metabolomic, proteomic, and trascriptiomic profile data (collectively "-omic" data) to establish relationships between interrelated biological pathways. In addition, PathExplore can offer several query options not offered by other systems, which permit a user to draw information from a variety of -omic data to quickly discern distinctions between relationships that are important from those that are not.

In a first aspect of the present invention, there are provided methods for determining a biological pathway based on a treatment of a biological specimen. The exemplary methods comprise the steps of: obtaining at least one profile generated from a treated biological specimen and determining whether the at least one profile contains information that matches with information associated with a reference biological pathway. The reference biological pathway comprises biological reactions obtained from a reference database having a plurality of records. Each of the records comprises a biological reaction containing molecules that are selected from among substrates and products. The profile is selectively obtained from a profile containing metabolic information in combination with a transcriptional profile and/or a proteomic profile.

In particular exemplary embodiments of the present invention, the method further comprises the step of selecting biological reactions from the reference biological pathway to determine the biological pathway based on the treatment of the biological specimen. In other exemplary embodiments of the present invention, the reference biological pathway is generated using a user-selectable criteria. For example, each of the records can include at least one product and at least one substrate associated with the biological reaction. In particular exemplary embodiments, each of the records further comprises information selected from among an enzyme and a free energy associated with the biological reaction. The reference biological pathway can be generated according to substeps of: (a) identifying at least one molecule; (b) searching the records of the reference database for information concerning the at least one molecule; (c) identifying which of the records has information concerning the at least one molecule; (d) identifying further molecules associated with the identified one or more records of substep (c); (e) searching the reference database to identify further biological reactions using the further molecules identified in substep (d); (f) linking the biological reaction of the identified records of substep (c) with the further biological reactions of substep (e) based on a common molecule to build a reference biological pathway, wherein the linking substep includes defining the product of the biological reaction as a substrate for a subsequently linked biological reaction; and (g) repeating substeps (b) to (f) until every record in the reference database is searched.

According to various embodiments of the present invention, the user-selectable criteria comprises an importance factor assigned to one or more substrates of the identified biological reaction located in the records of the reference database. The importance factor can determine whether the identified biological reaction associated with the substrate is to be eliminated to from the reference biological pathway. The user-selectable criteria may comprise an importance factor assigned to one or more products of the identified biological reaction located in the records of the reference database.

The user-selectable criteria can include a milestone value assigned to the molecule. The assignment of the milestone value may indicate that (i) the molecule is a start molecule at a start of the biological pathway, and/or (ii) the molecule is a stop molecule at an end of the biological pathway.

Various embodiments can further include the step of searching a second reference database comprising a plurality of records, each of the records containing information relating to a transporter biological reaction, wherein each of the records comprises a transporter protein, a molecule and an organelle. Each of the records can be assigned with a unique identifying number. The molecule may be assigned unique identifying numbers, in which one of the unique identifying numbers corresponds to the molecule at an external position and another one of the unique identifying numbers corresponds to the molecule at an internal position. Each of the records can further include information associated with a directionality of the transporter.

Each of the records may further comprise information associated with a subcellular localization of one of the product, the substrate, and an enzyme. Each of the molecules may also have a unique identifying number.

In other exemplary embodiments of the present invention, the transcriptional profile can be derived from microarray data generated from the treated biological specimen. The transcriptional profile may also be derived from microarray data generated from the treated biological specimen. The unique identifying number can correspond to a gene and an AFFYMETRIX™ ID number.

For example, the reference biological pathway may be queried using at least one external analytical tool. In one exemplary embodiment, the analytical tool is "AlignACE"™. Cis-acting genetic regulatory sequences responsive to various treatment conditions can be identified in such embodiments.

According to another aspect of the present invention, methods are provided for generating a biological pathway based on a treatment of a biological specimen. These methods similarly comprise the steps of: receiving at least one profile generated from a treated biological specimen; determining whether the at least one profile contains information that matches with information associated with a reference biological pathway; but also includes modifying the reference biological pathway to generate the biological pathway based on a treatment of a biological specimen. The reference biological pathway may comprise biological reactions obtained from a reference database having a plurality of records. Each of the records comprises a biological reaction containing molecules selected from among substrates and products, and at least one profile is selectively obtained from a profile containing metabolic information in combination with a transcriptional profile and/or a proteomic profile.

A third aspect of the present invention relates to computer implemented systems for accomplishing any combination of the forgoing methods. In certain embodiments, the systems are implemented over the Internet.

BRIEF DESCRIPTION OF THE DRAWINGS

FIG. 8 is a table that illustrates an example of a portion of output from a method provided herein when queried for pathways involved in glutamate biosynthesis.

FIG. 9 is a table that lists genes involved in two different methods for generating in vivo ammonia that were found to be induced by light using the method provided herein.

FIG. 10 is a table that lists results from analyzing the motifs found by AlignACE™ in the promoters of At1g64780, At3g21670 and At1g77760 in conjunction with the methods provided herein.

FIG. 11 is a table that lists motifs found by a random sampling of induced genes that were found to be statistically significant.

FIG. 12 is a table that shows that motif 14 from FIG. 11 was found to align with two portions of the known light response element GT -I.

FIG. 13 is a table that shows genes that contain motif 14 and their encoded proteins discovered by the methods provided herein. The genes were induced on both microarray chips in the accompanying Example.

DETAILED DESCRIPTION

General Description

Figure 1:
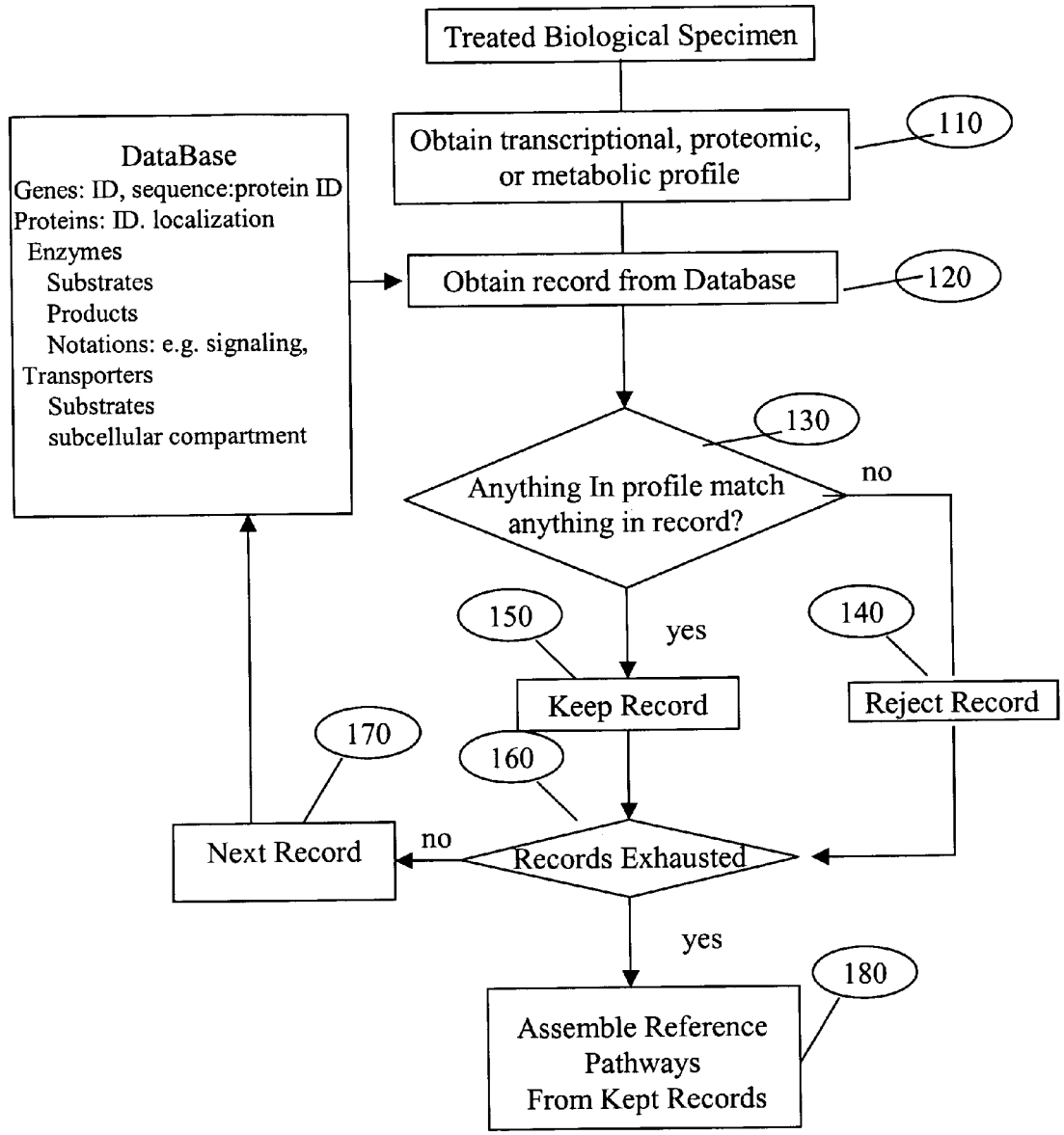
FIG. 1 is a flow chart depicting certain features of a method for building biological pathways from treatment data as provided herein.

The present invention relates to systems and processes for determining a biological pathway based on a treatment of a biological specimen implemented as a software arrangement herein referred to as "PathExplore." Exemplary steps in the process are depicted in the flow chart of FIG. 1. Data from treating a biological sample to test condition is obtained from any of a variety of sources in step 110. The source of data can be anything that includes records transcriptional, proteomic or metabolic information indicative of genes that are expressed, proteins that are expressed, or metabolic substrates and products produced by the biological specimen, respectively. In certain embodiments, the source of data is obtained from a microarray assay or other high throughput screening system that allows identification of the metabolic information. Once the metabolic profile is obtained, PathExplore accesses a Database in step 120 to compare the metabolic profile to known metabolic relationships. The database can include any a variety of information associated with records.

A record can contain, for example, the identity of genes associated with an ID number, the sequence of the gene, the name of the protein encoded thereby or other identification information for the protein. The record can contain the names of proteins identified by name or ID number, the subcellular location of the protein and/or other indicators as to the function of the protein. For example, the protein may be an enzyme, in which case the substrates and products of the enzyme are indicated in the record. The protein can be a transporter, in which case the subcellular compartment (membrane) in which the transporter resides is indicated, along with the substrate transported and optionally, the direction of transport as being into or out of the subcellular compartment. All of this type of information may be linked in a common record, or be dispersed in different records in the database.

In step 130 the metabolic profile data is compared to records in the database to determine if anything in the metabolic profile matches anything in a selected record in the database (i.e., includes the same gene, protein, substrate or product). If no match is found and the records in the database have not been exhausted, PathExplore takes the next record from the database and again looks for matches in step 140. Records that are matched are kept in step 150. PathExlpore can also continue to take the next record until all records have been exhausted in steps 160 and 170. The kept records are then used to assemble at least one, but more typically, all of the possible combinations of reference pathways in step 180. The reference pathways are arranged to link metabolites as substrates and products, to link enzymes or transporters that act on those substrates or products, and/or to further link the same to genes that encode the proteins.

Figure 2:
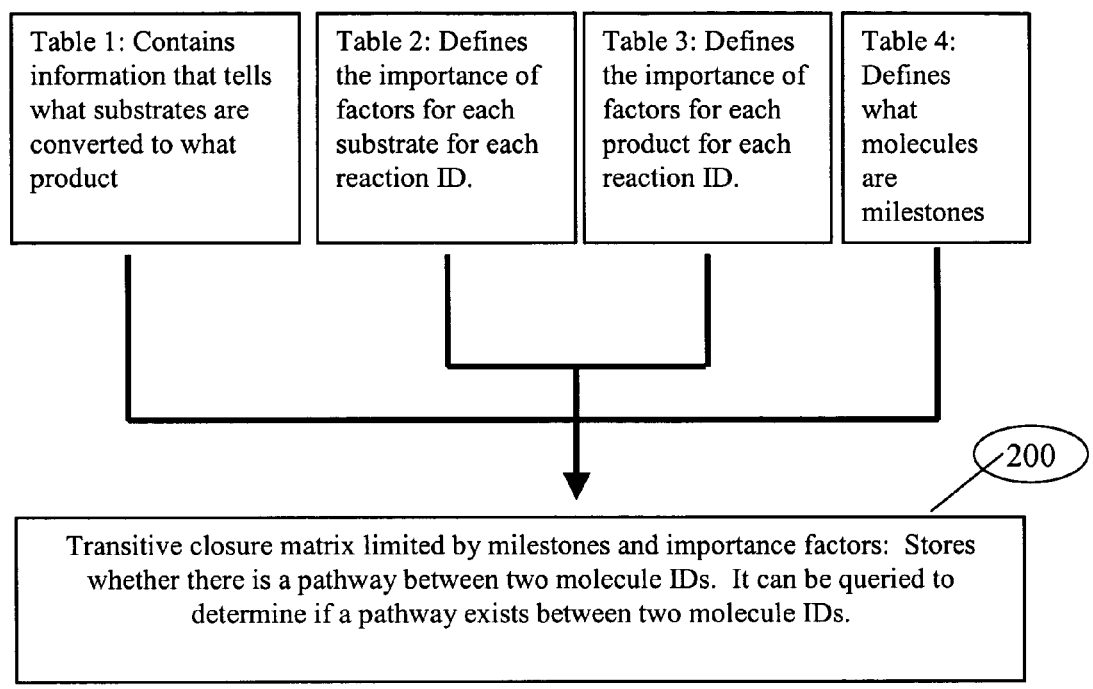
FIG. 2 is a diagram illustrating use of tables to implement certain features of the methods provided herein.

FIG. 2 illustrates an example of how PathExplore uses a transitive closure matrix to generate the reference biological pathway from the information found in the records. Such information may be assembled in tables, for example, as in Tables 1-4 of FIG. 2. The transitive closure process involves a query for information from one, some or all of the Tables. The user can select the molecule of interest. An initial step in the exemplary process according to an exemplary embodiment of the present invention can identify biological reactions for the reference biological pathway by querying Table 1, which is a database of biological reactions including substrates and products for the specific substrates or products that are selected by the user. Identified biological reactions having a common gene, protein or molecule can be linked to build the reference biological pathway. As mentioned above, in exemplary embodiments, the process continues until all records found in Table 1 are exhausted.

Figure 3:
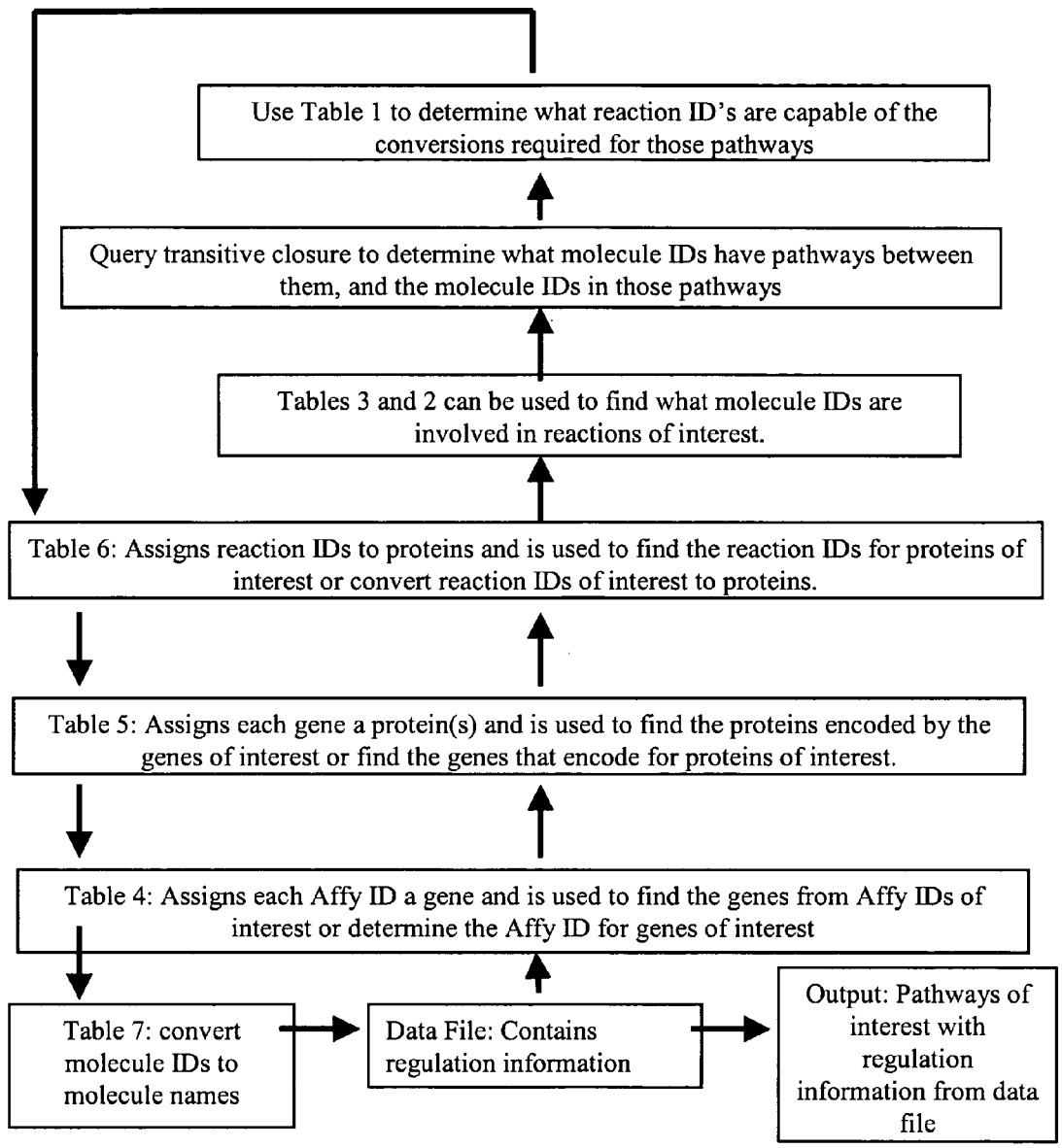
FIG. 3 is a diagram illustrating information flow for a query that asks: from a database to find pathways that fit transcriptosome data for genes of interest obtained from a metabolic profile from an AFFYMETRIX™ chip and IDs, and then to output pathways with relevant regulation data.

The transitive closure matrix may be used to store pathway information (step 200). If given two molecules, one can use the transitive closure matrix to ask if there are pathways between these two molecules (Information is stored in the transitive closure matrix with respect to molecule IDs). An example of how information from the database is used in a transitive closure matrix to assemble a reference biological pathway is depicted in FIG. 3. For example, Table 7 can contain relationships between molecule IDs and actual molecule names, and therefore can be used to convert molecule IDs to molecule names or vice versa, and to determine the other molecules involved in those pathways. The actual pathways do not necessarily have to be stored. A new transitive closure must be built anytime new pathways are added. There are transitive closures not limited by milestones or importance factors, limited by milestones but not importance factors, limited by importance factors but not milestones, and limited by both.

As indicated herein above, the extent of the reference biological pathway can be limited using transitive closure by the assignment of importance factors or milestones to the molecule of interest. The process involves querying information associated with Tables 2-3 for importance factors or milestones selected by the user. The extent of the reference biological pathway can also be limited by assignment of a score to relevant or desired biological reactions.

Figure 4:
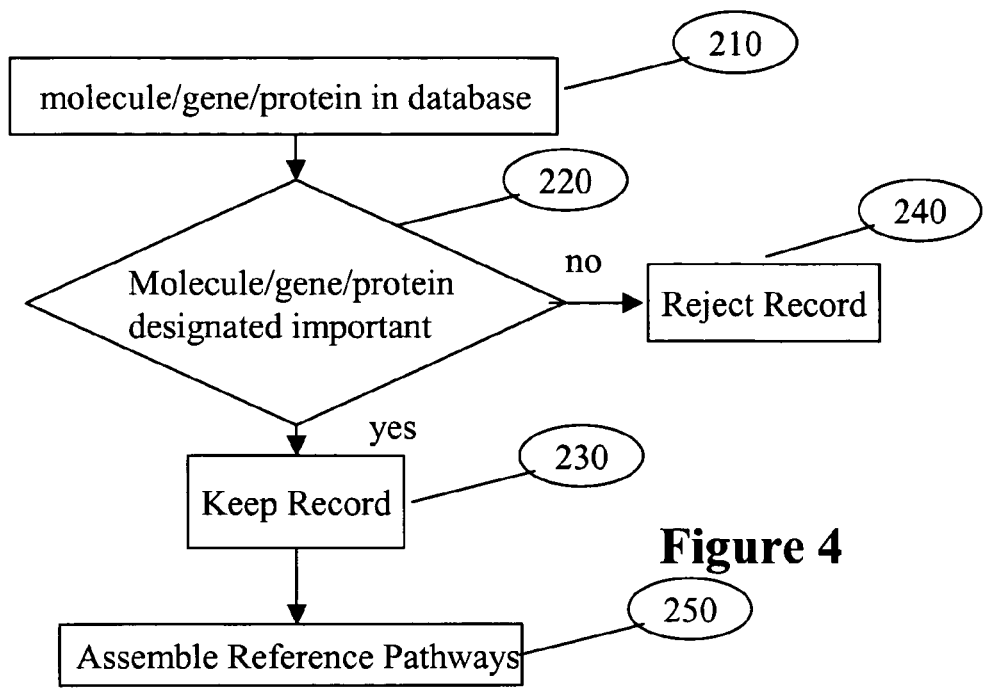
FIG. 4 is a flow chart that illustrates one example use of importance factors in the methods provided herein.
Figure 5:
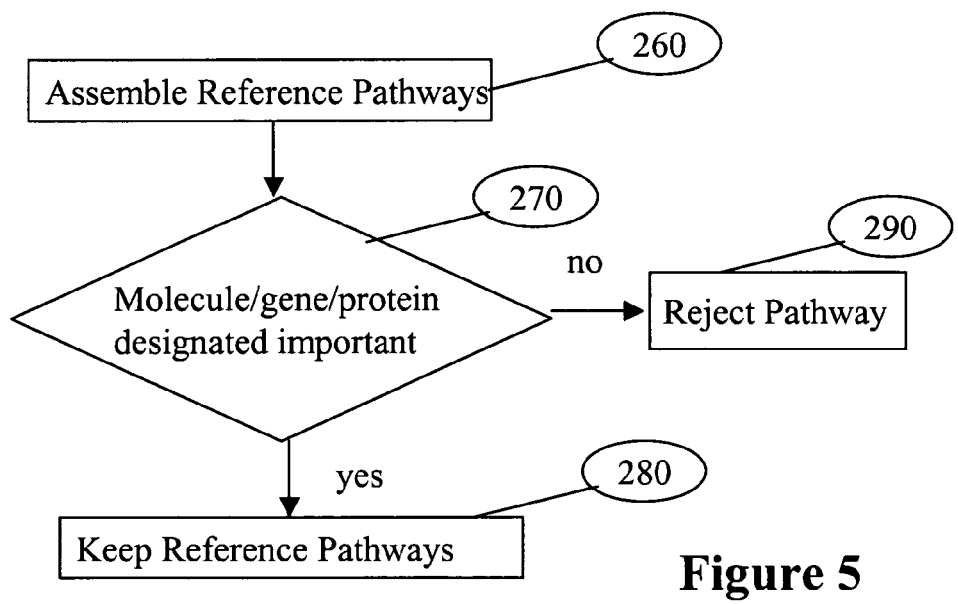
FIG. 5 is a flow chart that illustrates another example use of importance factors in the methods provided herein.

The importance factor can typically be a score assigned to a molecule of interest that is used by transitive closure to determine the biological relevance of the molecule of interest. The importance factor may also be used to determine whether an identified biological reaction is to be eliminated from or retained in the reference biological pathway. FIG. 4 shows a flow chart that illustrates one exemplary use of importance factors according to the present invention. Molecule/gene protein can be obtained in step 210. If the molecule of interest is assigned an importance factor by the user in step 220, PathExplore can keep those records that have appropriate importance factors (step 230), otherwise the record is rejected (step 240). The reference pathways are thus generated only from records that have an associated importance factor in step 250. FIG. 5 illustrates another way in which importance factors are used. In this embodiment, all the records that contain matches are kept and reference pathways are generated as in FIG. 1 (step 260). PathExplore can then examine the reference pathways, and determine if any includes a molecule that is designated important (step 270). It keeps those assembled reference pathways that contain molecules designated by the user to be important (step 280) and rejects those that do not (step 290).

Figure 6:
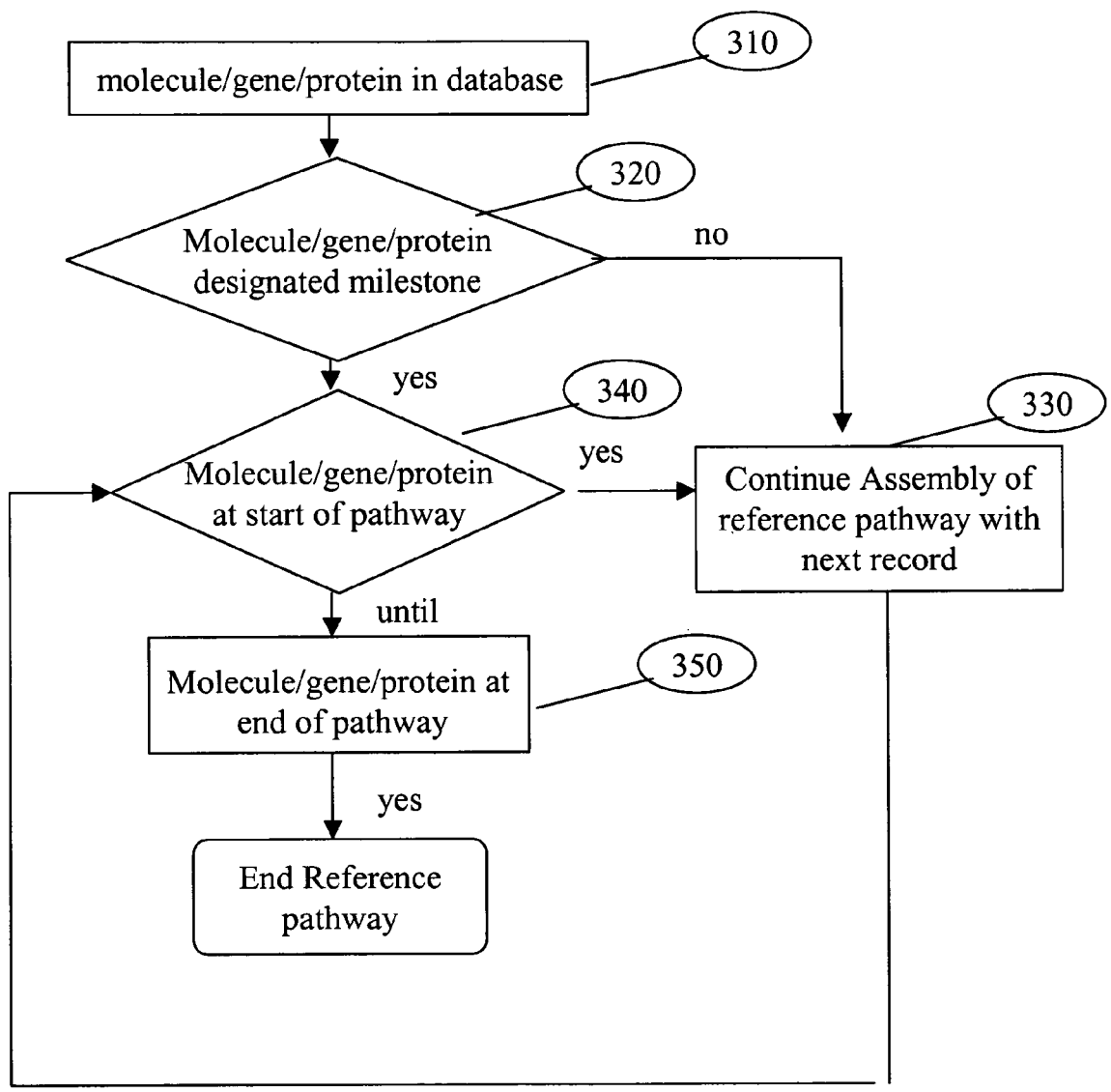
FIG. 6 is a flow chart that illustrates an example use of milestone designations in the methods provided herein.

FIG. 6 depicts one example of the use of a milestone. The milestone can be also a score assigned to a molecule of interest. The milestone can be defined as the molecule that is located at the beginning or end of a reference biological pathway. Initially, molecule/gene/protein can be obtained in step 310 if the molecule obtained from a kept record is not a milestone (step 340), PathExlpore will continue to assemble the reference pathway by linking to other records in the database (step 330). If the molecule of interest is designated a start milestone (step 340), PathExplore begins assembly of reference pathways outward from that molecule (step 350). If the molecule of interest is designated an end milestone, PathExplore will assemble reference pathways so as to end the assembled pathways with that molecule (step 350).

Genes, proteins and reactions may also be assigned scores, such as importance factors or milestones. The score is used to determine whether the gene, protein or reaction is to be eliminated from or retained in the reference biological pathway.

To determine a biological pathway based on a treated specimen, the reference biological pathway can be used as a backbone. Microarray data, metabolic data or protein data obtained from the treated specimen can be analyzed to query the reference biological pathway to select and determine the relevant biological pathways of interest based on a data profile from a treated specimen. Upon selection of the biological pathways based on the treated specimen, PathExplore can be used to identify relevant genes, proteins, and molecules in the pathway of interest.

PathExplore can also incorporate other analytical tools to identify other biological relevant entities, such as promoter elements. In the example described below, the presence of unregulated genes allows the identification of three genes involved in light-induced ammonia biosynthesis. The use of AlignACE™ in conjunction with genetic pathways obtained from PathExplore permitted analysis of upstream promoter elements in the identified genes and the identification of a promoter motif shared by other light-regulated genes.

A reference biological pathway using transitive closure can be rebuilt upon the selection of new criteria, e.g., milestones and importance factors, which can then be used to determine a biological pathway based on a treated specimen and subsequent additional queries for the identification of relevant genes, proteins, and molecules in the pathway of interest.

I. Assignment of Milestones, Importance Factors, and Conditionals.

The following example illustrates some of the features in a method for generation of biological pathways using importance factors and milestones according to one exemplary embodiment of the present invention. This example is based on the following set of reactions:

Rxn 1 takes A and produces B.
Rxn 2 takes B and produces C.
Rxn 3 takes C and produces D.
Rxn 4 takes D and produces both E and F.
Rxn 5 takes E and produces G.
Rxn 6 takes G and produces H.
Rxn 7 takes H and produces I.
Rxn 8 takes F and produces Z.
Rxn 9 takes Z and produces X.
Rxn 10 takes X and produces G.
Rxn 11 takes M and produce G.

The first step involves the designation of A as a molecule of interest and building a pathway comprising all possible reactions beginning with molecule A. A diagram depicting the reactions above may be illustrated as follows:

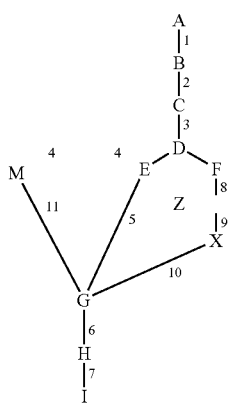

Milestones can be assigned at a global level, and therefore affect all pathways in the same manner. For example, assignment of G as an endpoint milestone in the above illustrated pathway, would result in two routes to G from A, one running through E and requiring reaction 5, and the second running through F and requiring reactions 8, 9, and 10. The identified reference biological pathway will not extend through G to H or I. Since milestones can be assigned globally, the system may not necessarily extend any pathway past G. For example, a query of the pathway to identify all molecules which could be made from E or M would result in G.

Additionally, importance factors can be introduced. Importance factors are generally assigned for every molecule in every reaction. Thus, it does not have a global effect as in the milestones described above. For example, E may be assigned as important and F as not important for Reaction 4. PathExplore may build a pathway running through E, but not F. A query of this pathway to identify all molecules which could be made from A would result in identification of B, C, D, E, G, H and I, which does not include any molecules from reactions which run through F.

In alternative embodiments of the present invention, importance factors and milestone may be assigned to genes, proteins or reactions.

The milestones and importance factors may also be combined in building the pathway. As an example, assignment of importance to E rather than F and G as an endpoint milestone would result in PathExplore building a pathway beginning at A, running through E, not F and ending at G.

The following example illustrates an assignment of importance factors for genes of interest where importance factors are placed on genes, rather than molecules. This example is based on the following set of reactions, each mediated by a gene that expresses a protein that catalyzes, or otherwise mediates the reaction:

1. Rxn 1 converts molecule A to B
2. Rxn 2 converts B to C
3. Rxn 3 converts C to D
4. Rxn 4 converts D to E
5. Rxn 5 converts D to F The relationship between these reactions may be pictorially depicted as follows:

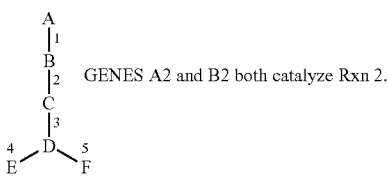

Rxn 2 is catalyzed by the product expressed by two genes, A2 and B2. An importance factor can be assigned to one or both of the genes. For example, A2 may be involved in the synthesis of molecule F, but E. Thus, A2 would be assigned as important, while B2 would be unimportant. In other words, when expression levels of gene A2 increase, expression levels of genes encoding for enzymes that catalyze Rxn 5 increase, and/or level of F itself increases. There is no relationship between the expression level of gene A2 and the biosynthesis of molecule E. By analyzing combinations of profile data containing transcriptome (microarray) and metabolite data, various queries can be performed using PathExplore.

To recognize the interrelationship of various proteins and enzymes, PathExplore is capable of assigning values to reactions in a Reaction Energy Table. In certain embodiments PathExplore can be used to assign conditional number to reactions. The information may reflect where one protein modifies the activity of another. For example, kinases can turn on or off an enzyme through phosphorylation. In plants, myrosinase can produce several products from the same starting molecule and the product produced is affected by myrosinase binding proteins.

Each reaction in a reaction energy table will be assigned a "conditional number." If the reaction occurs any time a gene for an enzyme is expressed, the reaction will be assigned a value of −1. If there is a conditional aspect to the reaction, then it will be assigned some other number. Listed in another table are the reactions with the necessary proteins, necessary conditions, as well as conditions in which the reaction could not occur.

To illustrate, an example of a kinase that phosphorylates nitrate reductase may be employed. Tables A and B below illustrate how if nitrate reductase and nitrate reductase kinase occur together, reaction 1.6.6.1 cannot occur and how conditional assignments and notations can be used with PathExplore:

TABLE A

| conditional restraint | reaction ID | enzyme |
|---|---|---|
| 1 | 1.6.6.1 | nitrate reductase [NADH/NADPH] |

TABLE B

| conditional restraint | necessary conditions | unpermitted conditions |
|---|---|---|
| 1 | ?? | nitrate reductase kinase |

II. Types of Queries Used to Identify Biologically Relevant Genes, Proteins and Molecules in the Pathway of Interest.

Several queries may be made using the pathways built by PathExplore. Returning to the first example pathway illustrated above, a query of this pathway to identify all molecules which could be made from A and pathways associated with these molecules would result in selection of a route running through E and identification of B, C, D, E and G. The data relating to the reactions, genes, and proteins can be also obtained. A similar query to select and identify all pathways which could be made from B would result in a similar route running through E, but would provide no information regarding A.

In a third query, a user can request the identification of all pathways which would result in the production of a molecule, e.g., G. The following three pathways may be identified:

1. M to G catalyzed by Rxn 11
2. A to G that runs through E
3. F to G, excluding Rxn 4.

Queries can also be performed using data derived from the data profile of a treated specimen. For example, the data profile may contain information regarding an induced gene which when expressed encodes a protein that catalyzes Rxn 3. PathExplore is capable of performing a query of the above pathway to identify routes to relate to this induced gene. PathExplore would identify Rxn 3 and molecules C and D. Additional queries can include the identification of all routes that produce C and D. Based on this example, PathExplore would identify pathways that start with A running through G and does not include F. PathExplore can query and select the pathway at the gene level and ask if there is a gene that meets a selected criteria. In this example, the criteria is induced expression of enzymes catalyzing Rxn 3. Similar queries can be performed at protein or molecule levels, or any combination of the three. PathExplore allows for the selection of relevant biological pathway for output based on the data in the profile from a treated biological specimen.

III. Reaction Identification Numbers

In an exemplary embodiment of the present invention, protein or enzymes catalyzing a reaction may also be involved in catalyzing reversible reactions. For example, branched chain amino acid aminotransferase catalyzes the conversion of valine to ketovaline and the reverse reaction, ketovaline to valine. In PathExplore, different reaction identification numbers are assigned to the forward reaction and the reverse reaction.

IV. Annotated Output Queries

PathExplore can also perform queries to produce output that contains annotations such as that described in the following example. This example also uses a branch chained amino acid aminotransferase, which catalyzes the conversion of valine to ketovaline. A branch chained amino acid aminotransferase that contains a mitochondrial localization signal may suggest localization of the enzyme to the mitochondria. However, the analysis of the possible paths that PathExplore can create showed that no other enzyme involved in the biosynthesis pathway of valine, or any other branch chained amino acid, is localized to the mitochondria. Furthermore, several enzymes that are involved in degradation of branch chained amino acids are localized to the mitochondria. Thus, it is not likely that the identified branch chained amino acid aminotransferase having a mitochondrial localization signal is an enzyme in the biosynthesis of valine.

Upon the identification of a branch chained amino acid aminotransferase having a mitochondrial localization signal, PathExplore can provide annotation that the identified enzyme may not have a role in valine biosynthesis. PathExplore generally does not eliminate such a gene, because conditions may exist where the identified gene does play a role in the pathway and the predicted localization signal is identified in error. An example of such information may be provided as follows, "Based on predicted subcellular localization we do not think that At1g10070 is involved in reaction 0.2.6.1.42."

Alternatively, each gene and molecule pair may be given a score based on relationship between the two in a grid format on a Table, wherein the Table has rows of molecules and the columns of genes. For example, if the gene is involved in reactions that have nothing to do with the synthesis of the molecule, it is given a value of 0. When the gene is involved in a reaction that is part of the route to the molecule, then it is assigned a value of 1. If there is no sufficient evidence (and therefore believe it is involved), the gene is assigned a value of 2.

Another table would list all the scenarios from this Table discussed in the above paragraph having a value of 1. Each entry would contain, inter alia, the gene, the molecule, and the annotated information. PathExplore would query these tables to generate the output.

V. Transporters

A. Up-Take Transporters

Up-take transporters are handled in a very simplistic way by the PathExplore system. A molecule external from the plant is given a molecule ID different than the same molecule that is internal (e.g. external nitrate 900024; nitrate 00024). Nitrate transporters involved in up-take can then be said to convert 900024 to 00024. The molecule that is external to the plant is always clearly labeled as such.

B. Intracellular Transporters

A plant cell is compartmentalized into several different unique compartments such as the nucleus, the mitochondria, and chloroplast. Membranes may used to separate the contents of the compartments from the bulk solution of the cell, which is called the cytoplasm. However, for some metabolic pathways to function small molecules must be transported in or out of a compartment to the cytoplasm and subsequently, at times, to another compartment. Therefore, these transporters are really part of the metabolic pathway and as such should be incorporated into pathways built into systems like PathExplore. Using a system and method described above for up-take transporters may be undesirable, because it would require giving many molecules different identification numbers based upon their localization whereas plants only up-take a limited number of molecules in a biologically relevant manner. Therefore, it is possible to design the system and method to take into account the localization of proteins and molecules when building the pathways. In order to perform such functions, three types of information can be used:

1. The localization of the proteins involved in pathways.
2. The specificity and directionality of the transporters.
3. The genes that encode for the transporters.

Protein localization is determined by a signal sequence in the protein. Since the sequence of every protein in Arabidopsis is known, the localization of every protein can be predicted. The predicted localization of every protein may be retrieved from the arabidopsis.org website. Information regarding the specificity and directionality of the transporters may be obtained from the literature. The literature can be used to determine what genes encode for what transporters. Some genes are also being assigned function based on sequence similarity. This information may be stored in two tables. For example, Table 10 assigns each transport "reaction" and ID. It identifies the proteins capable of carrying out that "reaction" and organelle involved in the "reaction" (a directionality is implied). Table 11 assigns a molecule(s) to the transport ID.

PathExplore can then be used to ask several different questions about intracellular transporter and their role in metabolic pathways. As a simple example, several genes in a metabolic pathway are induced and produces the following information:

1. Gene 1 catalyzes the conversion of molecule A to B and encodes a protein localized to the cytoplasm.
2. Gene 2 catalyzes the conversion of molecule B to C and encodes a protein localized to the cytoplasm.
3. Gene 3 catalyzes the conversion of molecule C to D and encodes a protein localized to the chloroplast.
4. Gene 4 catalyzes the conversion of molecule D to E and encodes a protein localized to the chloroplast.

Then, for this to be a functional pathway in the plant, there should be a transporter that transports molecule C into the chloroplast from the cytoplasm. The movement of molecule C can be verified based on the information in Table 10 and 11. If the movement is confirmed, then this "reaction" and the information about the genes and the proteins they encode (including -omic information) can be inserted into the pathway. If not, then the pathway can be rejected. Similarly, if a pathway is only in one compartment (including the cytoplasm), we can ask is it reasonable that the molecule that starts that pathway is in that compartment (i.e. is their an enzyme that produces that molecule in that compartment or is their a transporter to transport that molecule in to that compartment). PathExplore can be queried to include compartmentalization and intracellular transporter in the pathways or to ignore them. As such, it might be a useful tool in predicting what compartments and what molecules have intracellular transporters that have not yet been identified.

Figure 7:
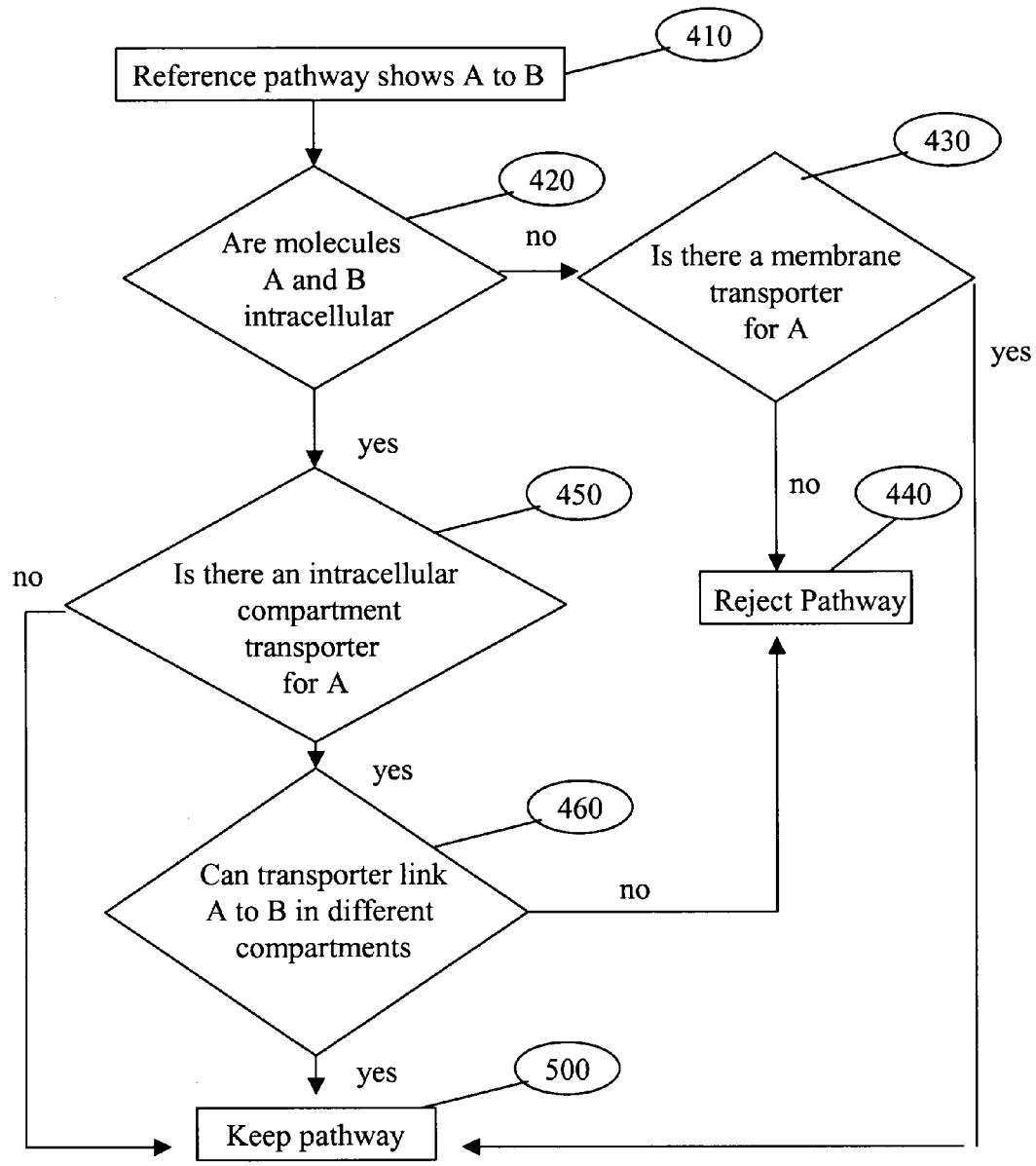
FIG. 7 is a flow chart that illustrates assembly of pathways where transporter proteins are involved.

FIG. 7 shows a flow chart that summarizes how transporter information is used in PathExplore according to an exemplary embodiment of the present invention. Assume a reference pathway is generated from the database showing a relationship between a "substrate" molecule A and a "product" molecule B (step 410). PathExplore can determine from the ID of these molecules whether or not they are intracellular or extracellular (step 420). If they are not intracellular, PathExlpore determines whether there is a cell membrane transporter for the substrate (step 430). If so, the reference pathway containing this relationship is kept (step 500), otherwise the pathway is rejected (step 440). If on the other hand, the molecules are intracellular, PathExlpore can query the database to determine if the there is any transporter for intracellular transport of A to another compartment (step 450). Alternatively or in addition, the user may designate the subcellular location of the molecules. If there is no such designation, and there are no transporters, both substrates are likely in the same compartment and the pathway is kept in step 500. Otherwise it is determined whether the transporter is located in an appropriate subcellular compartment having a transporter with an appropriate orientation to link A to B by transport, for example, by transporting A from the chloroplast to the cytoplasm where a second reaction converts A to B (step 460). If so the pathway is accepted, if not, the pathway is rejected in step 440.

Using PathExplore Features
Building Pathways

Two approaches are possible for building pathways. One is to define biochemical pathways and the corresponding enzymes therein as a static list. The other approach is to create a dynamic system that builds pathways from a database of reactions (including substrates and products), in which each reaction is linked to an enzyme and genes. A program can then build the pathways by linking the product of one reaction with the substrate of another. PathExplore can use the latter approach both because it is a more realistic representation of a biological system which allows connections between pathways that use common substrates and because it allows for greater flexibility and growth. The dynamic "build-the-pathways" method prefers every substrate to be paired with the product(s) that it is converted to during the reaction. One substrate can be assigned to multiple products, and one product can be assigned multiple substrates. The system can then perform a transitive closure based on the assignments of the substrate product relationships for each reaction. The transitive closure can then be used to answer queries asking for paths between two molecules, how to create a molecule, or what can be produced from a molecule.

Using the dynamic "build-the-pathways" method may pose some challenges that are solved by importance factors and milestones used with PathExlpore. For example, based on the reactions in the current database, PathExplore is capable of constructing more than 250 pathways to produce L-glutamate. In order to limit the pathways produced by PathExplore to those that are likely to be biologically relevant, every substrate and product in a reaction was assigned an importance (1=important and 2=not important). The importance of the substrates and products can be based on the function of the enzyme, and its role in metabolism. For example, for the reaction catalyzed by glutamine synthetase, the molecules glutamate and ammonia have each been assigned an importance of 1, while the molecules ATP, AMP, and inorganic phosphate have been assigned an importance of 2. The reason is that the main function of glutamine synthetase is the synthesis of glutamine (from glutamate and ammonium), while the breakdown of ATP is just the energy used to drive the reaction. By contrast, for the enzyme apyrase, whose main function is the dephosphorylation of ATP to AMP and inorganic phosphate, the molecules ATP, AMP, and inorganic phosphate have been assigned an importance of 1. These types of rankings allow the system to be limited to the paths that can be constructed using substrate product pairs that are important.

Even with the importance filter, PathExplore is still able to construct 75 pathways to make L-glutamate, the longest of which is 120 steps. To reduce path lengths, the molecules that play a central role in metabolism were designated as "milestones". As a default option, PathExplore can be designed to begin and end pathways when they reach either a milestone or a molecule in the query. Querying PathExplore with milestones and importance factors resulted in 3 routes to make L-glutamate rather than the original 250 as shown in the upper part of the table depicted in FIG. 8. The output also includes summary tables for each -omic profile available in the analysis (not shown). The -omic profile results shown here are the result of an analysis of two data sets for each -omic profile. The data used to generate this Figure was test data, not actual experimental data. The gene regulation, protein value, and molecule value are based on criteria selected by the user. Genes, molecules, and proteins can be called induced (I), depressed (D), or not changed (NC) based on the -omic profile data, also when multiple data sets are analyzed, proteins, molecules, and genes that do not fall into the same category for all the data sets are marked IC (inconsistent). An item not in the profile is marked NP (not present). The regulation of each item also includes a tag P for protein, G for gene, or M for molecule so the user can easily identify which type of item is being described.

With these filters, PathExplore is capable of generating the biologically most relevant pathways. In this case, the pathways generated for glutamate biosynthesis by PathExplore are also in KEGG as described in Kanehisa, M. et al., "The KEGG databases at GenomeNet," Nucleic Acids Res. 30:42-46, 2002. While the use of importance and milestones is the default, PathExplore does have functions that allow the user to disregard the milestones and/or importance factors, thus trading relevance for completeness in the queries. PathExplore also offers the user the ability to modify the milestones and the importance factors to reflect the user's interest (this is discussed in further detail below).

In the glutamate example, where three possible glutamate synthesis pathways are shown, PathExplore has found a pathway that is a single enzymatic step. This demonstrates the influence of the milestones on the default behavior of PathExplore. PathExplore has reference to reactions that are involved in L-glutamine biosynthesis, yet when queried about the biosynthesis of L-glutamate, those reactions are absent because Lglutamine is a milestone and PathExplore begins synthesizing pathways at milestones. Pathways one and two represent two intersecting pathways. Both pathways contain a molecule necessary for the biosynthesis of L-glutamate by glutamate synthase, so the last step (the synthesis of L-glutamate) is catalyzed by the same enzymes in each case. This can be determined because the reaction ID in both cases may be 1.4.1.13 or 1.4.7.1; the only way for this to occur is if the chemical reactions are completely identical. The third pathway synthesizes glutamate from the degradation of glutathione. The role of this pathway in glutamate metabolism is unknown at this time, however glutathione is thought to be used to store cysteine in plants. This pathway demonstrates the ability of PathExplore to identify and group pathways that are not normally classified together in a classical biochemical pathway sense (KEGG does not include glutathione degradation in the same map as the rest of glutamate metabolism (7)). As explained below, PathExplore further allows one to compare the regulation of the genes encoding these glutamate biosynthetic proteins using micro array data, thus providing insight into the possible role of each of these pathways for glutamate synthesis under different growth conditions.

Exemplary Contents of PathExplore

A user may assign information regarding a gene, a reaction or substrate using any nomenclature suitable for use with an appropriate database, instrument output or other for of data output. In one example embodiment of the present invention, an AFFYMETRIX™ ID to a gene, a gene to an enzyme(s), and an enzyme to a reaction(s) may be assigned. To avoid confusion, the official NCBI gene names resulting from the complete sequencing of *A. thaliana* were used for gene names. The system may also be designed to hold other information about the gene including a common name (i.e. Nrt2.2). The assignment of a gene to an enzyme can be accomplished by reviewing the literature and from the annotation of genes by NCBI. In the one exemplary version of PathExplore, approximately 23,400 genes can be assigned a protein name or description resulting in over 400 biochemical reactions. This number can constantly be increased by the addition of new data as it becomes available. For every protein, PathExplore may also be designed to contain information about its sub-cellular localization, and for every reaction, it can contain the free energy of the reaction where available. To assign reactions to proteins, it may be preferable to give every reaction a unique identifier. In all possible cases, the enzyme commission number can be used. However in some cases (such as nitrate symporters) there was no enzyme commission number to describe the activity of the enzyme, so a unique number was assigned. It may also be preferable to assign a unique number to every molecule in each reaction. In one exemplary embodiment of the present invention, in all possible cases the number already assigned to that molecule by the LIGAND™ database can be used as described in Goto, S. et al., "LIGAND: Chemical Database for Enzyme Reactions," Bioinformatics 14:591-599, 1998. Some molecules that have been entered into PathExplore may not be in LIGAND™. In those cases, a unique number can be assigned to each of those molecules.

Using PathExplore to Query -omic Profiles

The Web Version of PathExplore

PathExplore is available online. In one exemplary embodiment, PathExplore can query microarray expression data to find induced genes or proteins having induced genes based on AFFYMETRIX™ ID's. It can also be used to determine which genes encode for which enzymes, and various other similar queries. Since one exemplary embodiment of PathExplore was designed to use expression data from AFFYMETRIX™ chips analyzed by the AFFYMETRIX MICROARRAY SUITE™ software, some of the calls generated by the AFFYMETRIX™ software can be used in the analysis of expression data. However, PathExplore can also use a numerical value, so that data generated by non-AFFYMETRIX™ chips can be analyzed. For users not studying Arabidopsis, PathExplore can analyze data regarding any organism if the user up-loads a file containing the relationships between genes and enzymes (like that discussed above) for the genes in that organism. A simpler analysis is also possible, in which PathExplore can determine all of the biochemical pathways to which a list of molecules, enzymes and/or *A. thaliana* genes belongs, which may be useful if PathExplore is used in conjunction with another type of analysis (such as clustering).

As discussed above, PathExplore has been designed to allow queries for the pathways of interest, and one method of selecting a set of biochemical pathways is by querying for those pathways that share a molecule of interest. When analyzing expression data, it is also possible to select biochemical pathways based on the expression of at least some of the genes in the pathway. PathExplore can find all the pathways that contain an enzyme for which at least one gene in the pathway meets a user selected criterion with regard to its transcriptional state (or one molecule or one protein with regard to its in vivo level). The program then displays those pathways based on the number of steps that have an item (gene, protein or molecule) that match the user selected criteria.

The "retrieved" pathways can then be grouped or filtered by several criteria, including by way of example:
1. Pathways that start at the same molecule.
2. Pathways that end at the same molecule.
3. Pathways that have enzymes that use or produce the same molecule.
4. Pathways that contain the same proteins.
5. Pathways that share the sub-cellular compartmentalization of at least one regulated protein.

These groupings can allow the user to find relationships between co-regulated pathways. For example, PathExplore finds eleven molecules that can be made from the milestone L-glutamate. Since L-glutamate is a milestone, PathExplore would not, by default, include the biosynthesis of L-glutamate in the pathways to make these molecules, but by grouping the pathways by which molecules they start with and end with, the user can easily identify conditions in which L-glutamate biosynthesis (pathways that end in L-glutamate) and the biosynthesis of some of its down-stream metabolites (pathways that start with L-glutamate) are co-regulated.

Personalizing the Pathways Made by PathExplore

In addition to offering users the ability to change defaults with regard to importance factors and milestones for some functions, PathExplore can allow the user to upload new importance and milestone or even substrate-product-reaction information.

Since the transitive closure encompasses the information contained in the milestones and importance factors, this allows users to change the behavior of the entire system.

Other Exemplary Aspects of PathExlpore

While PathExplore is designed to analyze proteomic and metabolomic data as well as gene expression data, it seems likely that in the short term (until there is more proteomic and metabolomic data) its primary use will be to analyze gene expression data as do the PathDB/ISYS/MaxdViewer and AraCyc systems. Each system has a different approach to processing and presenting the data. AraCyc uses a "metabolic map" approach to presenting the gene expression data with respect to the biochemical pathways. For example, the "metabolic map" generated by AraCyc contained essentially the same routes to the biosynthesis of six of the eleven molecules found to be downstream metabolites of L-glutamate (e.g. chlorophyll, L-glutamine, glutathione, L-arginine, L-proline, and heme). However, in contrast to the results obtained with PathExplore, for all six of these pathways, the AraCyc metabolic map failed to make a connection between these pathways and L-glutamate biosynthesis. This is very understandable due to the complexity and interconnections of metabolic networks: it is impractical to graphically display all of the connections.

PathExplore itself (by using milestones and the importance factors of substrates and products) can limit the connections between pathways in order to ensure that biologically relevant pathways are made. However, PathExplore can also group or filter the pathways to allow the user to discover pathways that are related (e.g. have the same starting molecule). While a graphical metabolic map such as the one displayed in AraCyc can give a quick clear visual sense of the regulation of metabolic pathways, it does not easily give the detailed information necessary for some analysis. Since PathExplore can be selectively synthesizing pathways of interest based on queries and profile data, it is able to make more connections between pathways and give more information about those pathways than a graphical "metabolic map" approach. While PathExplore and AraCyc may be web-based tools, the PathDB/ISYS/MaxdViewer system is JAVA based and requires the down load of the three programs to be run locally. PathDB/ISYS/MaxdViewer contains tools beyond those necessary to analyze gene expression data with respect to biochemical pathways such as several different clustering algorithms and ways of graphing/visualizing the data. PathExplore is, in-fact, complementary in that PathDB has a graphical interface and many tools, whereas PathExplore has the five benefits described above, that include:

1. Multiple path options (milestones and importance factors that can be used or ignored).
2. The ability to modify PathExplore via uploads of files.
3. A universal web-based interface requiring no downloads.
4. A text input and output that allows it to be used easily with other tools.
5. The ability to easily filter or group pathways based on several characteristics.

PathExplore's design is flexible and can be adapted to regulatory pathways (see below). As described above, PathExplore can contain information regarding transport proteins and their passenger molecules and can build pathways involving transporters or symporters as illustrated below. Such things are not normally included in biochemical databases and do not appear to be included in pathways by the AraCyc or PathDB/ISYS/MaxdViewer systems.

The K Interface Version of PathExplore

In one exemplary embodiment, the "work" or "synthesis" performed by PathExplore can be accomplished using an array-based programming language called K. K can be down loaded online, and the files necessary to run PathExplore locally can be made available upon request. The local version of PathExplore has more functionality than the web-based version above and can be queried using basic SQL in addition to the already existing functions. Users would also then have complete privacy for their data.

Example I

The Use of PathExplore to Define Mechanisms of Gene Regulation

In order to test the usefulness of PathExplore in gene regulation discovery, sample microarray data was analyzed. Two microarray chips were used to analyze RNA isolated from *A. thaliana* treated under identical conditions except for the presence or absence variations of light. The results of the microarray chips were analyzed with AFFYMETRIX SUITE 4.0™. For each condition, a biological replicate was also analyzed (a total of four total microarray chips). The results for both biological replicates (light-treated vs. dark) were then analyzed with PathExplore to identify genes involved in amino acid biosynthesis that were regulated by light. Ammonia, which is a milestone, was included in this analysis, because it plays a key role in glutamine biosynthesis. This analysis indicated that three genes involved in pathways that could be considered "de novo" ammonia "biosynthesis" were all induced by light, which are depicted in the table of FIG. 9. These genes were found in the two different pathways to "make" ammonia. In order to identify cis-elements that are common to the promoters of these three light regulated genes, the motif discovery tool called AlignACE™ was used as described in Hughes, J. D. et al., "Computational Identification of Cis-regulatory Elements Associated with Groups of Functionally Related Genes in *Saccharomyces cerevisiae*," J. Mol. Biol. 296:1205-1214, 2000. AlignACE™ found fifteen motifs shared by these 3 promoters, which are depicted in FIG. 10. Motif names were found by searching Plant Care with the sequence found by AlignACE™ Sequences not found in Plant Care were assigned a number. Transcription correlation statistics were calculated as describe din Materials and Methods for the sequence found by AlignACE™. A p-value of less than 0.05 was considered significant. No gene in the genome contained more than 2 copies of motif 15, therefore, there were no genes with a high copy number of motif 15 to analyze.

Materials and Methods

A. Motif Prediction

Up-stream sequences up to I KB from the ATG start site were obtained using RSA tools, sequences which overlapped with open reading frames were not selected. The program AlignACE 3.0™ was used to predict sequences that were overrepresented in our promoter sets. Since AlignACE™ is based on a Gibbs Sampling Algorithm, three runs using the same parameters on the same promoter sequences were done so as not to miss any weak motifs (10). For each particular promoter set the parameters "columns to align" and "fraction background GC content" were kept constant at 7 and 0.364, respectively. The parameter "number of sites to expect" was varied by 5, 6 and 9. The large number of motifs produced by AlignACE™ for each promoter set were narrowed down in two ways:

1) Any motif in which the only conserved bases were adenosines were removed.

2) Motifs that were found in more than one run were counted only once.

IUPAC degenerate code was incorporated into each motif based upon the bases found at a particular position, and genes that contained these motifs in their promoter (1 KB from the start) were obtained using RSA tools (12). The regulation of the genes that contained each motif were then analyzed to determine if the motif had an affect on transcription. In addition to analyzing all the genes that contained the motif, for each motif all of the genes were broken down into two categories: genes with a low copy number of the motif (genes that contained less than 4 copies of the motif) and genes with a high copy number of the motif (genes that contained 4 or more copies of the motif). Each one of these sub-groups were also analyzed to determine if the motif affected transcription.

B. Determination of the Role for Each Motif on Gene Regulation.

The genes on the chip were grouped into one of four categories based on the AFFYMETRIX™ calls. Induced genes were genes that were called present and induced in both replicates, repressed genes were called present and repressed in both replicates, not changed genes were genes that were called not changed and present in both replicates, and inconsistently regulated genes were genes that were not called the same thing in the AFFYMETRIX™ analysis (e.g. induced in one replicate, but not changed in the other) or called absent in both or one replicates. A p-value for induction was calculated by using a standard binomial test to compare the number of induced genes to the number of consistently regulated (induced, repressed, and not changed) genes for each grouping and comparing it to the percentage of induced genes out of the consistently regulated genes for the whole chip as described in Ross, S., "A First Course in Probability," Prentice Hall, Upper Saddle River, N.J., 1998. Groups with a p-value less 0.05 were considered to statistically favor induction.

C. Results

The cis-motifs were analyzed in two parallel ways. First, "PlantCare" was queried with each motif to determine if it was a known motif as described in Lescot, M. et al., "PlantOARE, a database of plant cis-acting regulatory elements and a portal to tools for in silico analysis of promoter sequences," Nucleic Acids Res. 30:325-327, 2002. Second, the upstream sequences of all the genes in the Arabidopsis genome were searched for the presence of each motif using the RSA tools website as described in Van Helden, J. et al., "Extracting regulatory sites from the upstream region of yeast genes by computational analysis of oligonucleotide frequencies," J. Mol. Biol. 281:827-842, 1998. The expression of those genes that are on the AFFYMETRIX™ microarray chip (8,000 gene version) were analyzed to determine if the genes that contained each motif differed in the percentage of induced genes in a statistically meaningful manner when compared to the rest of the population.

Several of the motifs were found to be known light-response elements based on previous experimental analysis which are illustrated in the table of FIG. 10. However, motif 14 appears to be the most important motif found in regulating these three genes under the conditions tested. Two pieces of evidence support the functionality of motif 14. 1) Of all the motifs uncovered, only motif 14 was found to statistically favor induction in the genome-wide promoter analysis at the amount of copies found in all three original genes (FIG. 10). Of all the motifs tested, none gave a larger proportion of induced genes in the genome wide promoter analysis as shown in FIG. 10.

To determine the value of PathExplore in this study, the occurrence of motif 14 in the promoters of the complete genome was determined. Motif 14 was found in 1649 genes of which only 211 were on the microarray chip and consistently expressed. Further analysis found that motif 14 was found only at low copy numbers (There are only five genes in the microarray chip that have 2 copies of motif 14, and no gene on the microarray chip has more than 2 copies.). However all three of the genes that were used for the analysis contained motif 14, and two of them contained two copies of motif 14, while less than 10% of all the induced genes contained motif 14. This shows that PathExplore revealed a pathway having an enrichment of genes that contained motif 14 when compared to the whole microarray chip or even all of the induced genes. The significance of motif 14 when compared to genes generated from three sets of three randomly selected light-induced genes was also analyzed. While some of the motifs that were found using the random genes were found to be statistically significant, none were more significant than motif 14 as indicated in the table of FIG. 11, and in no random case was motif 14 uncovered. This indicates that the PathExplore analysis is more valuable than merely grouping genes by expression profile.

Motif 14 was analyzed further. It was found that motif 14 aligns well with motif 13 and also with GT-1, a previously validated light response element as shown in the table of FIG. 12. Interestingly, motif 13 was also found to be statistically significant for light-induction when present at high copy in the genome wide analysis. The conserved sequences in motifs 13 and 14 and GT-1 (TGTGG and GDTTG) were used to search the PlantCare database (see Lescot, M. et al., "PlantCARE, a database of plant cis-acting regulatory elements and a portal to tools for in silico analysis of promoter sequences," Nucleic Acids Res. 30:325-327, 2002). These conserved sequences were not only found in several known light response elements, but were also found to be the conserved part of some light response elements across a number of species. Genes that contained each one of these smaller motifs were identified, and their affect on the percentage of induced genes in the genome wide analysis was determined. GDTTG was not found to have a statistically meaningful affect on light-induction, while genes that contained a high number of copies of TGTGG had statistically more induced genes than expected by random chance in the genome wide promoter analysis (results not shown). This study therefore adds evidence to the role of TGTGG containing motifs in the light regulation of genes.

The proteins encoded by other genes whose also promoters contain motif 14 and were induced were identified and are depicted in the table of FIG. 13. This list suggests a role for motif 14 in the regulation of a large number of processes due to light, including possibly a further role in ammonia metabolism since one of the enzymes is glutamine synthetase, which incorporates inorganic nitrogen (NH3) into an organic form (glutamine).

The foregoing Examples and description are merely representative of exemplary embodiments and uses of PathExplore. With the rapidly increasing use of micro array technology and genomics by scientists to study a diverse array of topics, it is evident that tools necessary to mine large amounts of data need to be built. PathExplore allows for the easy generation of "systems" relevant data from metabolite profiles, and/or micro array experiments, and/or proteome studies in a way that is complementary to existing systems. As an example application, PathExplore has determined which amino acid biosynthetic pathways are regulated by light. This analysis tested a hypothesis: co-transcribed genes in the same pathway will share cis-regulatory elements. The PathExplore analysis found genes in pathways that share a product and that were induced. The analysis of the promoters of these three genes with AlignACE™ identified several known light-response elements, which strongly indicates that the three genes in our analysis might share common regulatory mechanisms.

Such an analysis is particularly easy in PathExplore, but this is just one example of many analyses that it could be used for.

PathExplore is capable of being implemented with new kinds of pathways. For example, the PathExplore database can be expanded to include non-metabolic "pathways" such as signaling cascades. Also, PathExplore can be modified to take in information regarding the phenotypic state of the plant and couple that with -omic profile data to determine what molecular changes were associated with a particular phenotype.

From the foregoing it will be appreciated that, although specific embodiments of the invention have been described herein for purposes of illustration, various modifications may be made without deviating from the spirit and scope of the invention. Accordingly, the invention is not limited except as by the following claims. All information provided by and associated with the references, links and products cited above are incorporated herein by reference in their entireties.

What is claimed is:

1. A computer-readable medium having stored thereon computer-executable instructions for determining a biological pathway based on a treatment of a biological specimen, wherein, when the instructions are executed by a processor, the following procedures are performed, the procedures comprising:

obtaining at least one profile generated from a treated biological specimen;

determining whether the at least one profile contains information that matches with information associated with a reference biological pathway; and generating the reference biological pathway using a user-selectable criterion and based on the matched information;

wherein the reference biological pathway comprises biological reactions obtained from a reference database having a plurality of records, wherein each of the records comprises a biological reaction containing a plurality of molecules, wherein the user-selectable criterion comprises an importance factor assigned to one or more products of the biological reactions located in the records of the reference database, and wherein the plurality of molecules are selected from among substrates and products.

2. The computer-readable medium of claim 1, wherein the reference biological pathway is generated using a transitive closure matrix.

3. The computer-readable medium of claim 1, wherein each of the records comprises at least one product and at least one substrate associated with the biological reaction.

4. The computer-readable medium of claim 3, wherein each of the records further comprises information based on at least one of an enzyme or free energy associated with the biological reaction.

5. The computer-readable medium of claim 3, wherein the reference biological pathway is generated by:
(a) identifying at least one molecule;
(b) searching the records of the reference database for information concerning the at least one molecule;
(c) identifying which of the records has information concerning the at least one molecule;
(d) identifying further molecules associated with the identified one or more records of (c);
(e) searching the reference database to identify further biological reactions using the further molecules identified in (d);
(f) linking the biological reaction of the identified records of (c) with the further biological reactions of (e) based on a common molecule to build a reference biological pathway, wherein the linking substep includes defining the product of the biological reaction as a substrate for a subsequently linked biological reaction; and
(g) repeating (b) to (f) until every record in the reference database is searched.

6. The computer-readable medium of claim 1, wherein the importance factor determines whether the identified biological reaction associated with the product is to be eliminated from the reference biological pathway.

7. The computer-readable medium of claim 5, further comprising searching a second reference database comprising a plurality of records, wherein each of the records contains information relating to a transporter biological reaction, and wherein each of the records comprises a transporter protein, a molecule and an organelle.

8. The computer-readable medium of claim 7, wherein each of the records is assigned a unique identifying number.

9. The computer-readable medium of claim 7, wherein the at least one molecule is assigned further unique identifying numbers, wherein one of the further unique identifying numbers corresponds to the at least one molecule at an external position and another one of the further unique identifying numbers corresponds to the at least one molecule at an internal position.

10. The computer-readable medium of claim 7, wherein each of the records further comprises information associated with a directionality of the transporter.

11. The computer-readable medium of claim 1, wherein each of the records is assigned a unique identifying number.

12. The computer-readable medium of claim 1, wherein each of the records further comprises information associated with a subcellular localization of one of the product, the substrate, and an enzyme.

13. The computer-readable medium of claim 1, wherein each of the plurality of molecules has a unique identifying number.

14. The computer-readable medium of claim 1, wherein the at least one profile is obtained from microarray data generated from the treated biological specimen.

15. The computer-readable medium of claim 13, wherein the at least one profile is obtained from microarray data generated from the treated biological specimen.

16. The computer-readable medium of claim 15, wherein the unique identifying number is based on a gene and an identification number.

17. The computer-readable medium of claim 1, wherein the at least one profile is selectively obtained from a profile containing metabolic information in combination with at least one of a transcriptional profile and a proteomic profile.

* * * * *

SEQUENCE LISTING

```
<160> NUMBER OF SEQ ID NOS: 26

<210> SEQ ID NO 1
<211> LENGTH: 7
<212> TYPE: PRT
<213> ORGANISM: Saccharomyces cerevisiae

<400> SEQUENCE: 1

Ala Gly Arg Ala Gly Ala Ala
1               5

<210> SEQ ID NO 2
<211> LENGTH: 10
<212> TYPE: DNA
<213> ORGANISM: Saccharomyces cerevisiae

<400> SEQUENCE: 2
gagaagaata                                                          10

<210> SEQ ID NO 3
<211> LENGTH: 9
<212> TYPE: PRT
<213> ORGANISM: Saccharomyces cerevisiae

<400> SEQUENCE: 3

Cys Asn Asn Ala Ala Ala Cys Met Ala
1               5

<210> SEQ ID NO 4
<211> LENGTH: 9
<212> TYPE: DNA
<213> ORGANISM: Saccharomyces cerevisiae

<400> SEQUENCE: 4 ccaaaacca                                                            9

<210> SEQ ID NO 5
<211> LENGTH: 10
<212> TYPE: PRT
<213> ORGANISM: Saccharomyces cerevisiae

<400> SEQUENCE: 5

Ala Cys Cys Ala Met Ala Asn Asn Asn Ala
```

<210> SEQ ID NO 6
<211> LENGTH: 14
<212> TYPE: DNA
<213> ORGANISM: Saccharomyces cerevisiae

<400> SEQUENCE: 6
ttaccacaga aacc                                                        14

<210> SEQ ID NO 7
<211> LENGTH: 8
<212> TYPE: PRT
<213> ORGANISM: Saccharomyces cerevisiae

<400> SEQUENCE: 7

Ala Ala Ala Asn Ala Ala Trp Thr
1               5

<210> SEQ ID NO 8
<211> LENGTH: 10
<212> TYPE: DNA
<213> ORGANISM: Saccharomyces cerevisiae

<400> SEQUENCE: 8
aaaaaatttc                                                             10

<210> SEQ ID NO 9
<211> LENGTH: 7
<212> TYPE: PRT
<213> ORGANISM: Saccharomyces cerevisiae

<400> SEQUENCE: 9

Cys Ala Met Trp Cys Ala Ala
1               5

<210> SEQ ID NO 10
<211> LENGTH: 12
<212> TYPE: DNA
<213> ORGANISM: Saccharomyces cerevisiae

<400> SEQUENCE: 10
caatcaaaac ct                                                          12

<210> SEQ ID NO 11
<211> LENGTH: 7
<212> TYPE: PRT
<213> ORGANISM: Saccharomyces cerevisiae

<400> SEQUENCE: 11

Gly Trp Gly Lys Thr Thr Gly
1               5

<210> SEQ ID NO 12
<211> LENGTH: 11
<212> TYPE: DNA
<213> ORGANISM: Saccharomyces cerevisiae

<400> SEQUENCE: 12
atggtggttg g                                                           11

<210> SEQ ID NO 13
<211> LENGTH: 8
<212> TYPE: PRT

```
<213> ORGANISM: Saccharomyces cerevisiae

<400> SEQUENCE: 13

Ala Arg Asn Gly Trp Gly Ala Gly
1               5

<210> SEQ ID NO 14
<211> LENGTH: 9
<212> TYPE: PRT
<213> ORGANISM: Saccharomyces cerevisiae

<400> SEQUENCE: 14

Cys Asn Ala Ala Ala Ala Asn Asn Ala
1               5

<210> SEQ ID NO 15
<211> LENGTH: 8
<212> TYPE: PRT
<213> ORGANISM: Saccharomyces cerevisiae

<400> SEQUENCE: 15

Ala Ala Ala Asn Cys Ala Ala Ala
1               5

<210> SEQ ID NO 16
<211> LENGTH: 7
<212> TYPE: PRT
<213> ORGANISM: Saccharomyces cerevisiae

<400> SEQUENCE: 16

Gly Arg Gly Ala Arg Gly Gly
1               5

<210> SEQ ID NO 17
<211> LENGTH: 7
<212> TYPE: PRT
<213> ORGANISM: Saccharomyces cerevisiae

<400> SEQUENCE: 17

Cys Ala Cys Ala Ala Ala Met
1               5

<210> SEQ ID NO 18
<211> LENGTH: 11
<212> TYPE: PRT
<213> ORGANISM: Saccharomyces cerevisiae

<400> SEQUENCE: 18

Gly Trp Gly Asn Asn Gly Ala Gly Asn Asn Ala
1               5                   10

<210> SEQ ID NO 19
<211> LENGTH: 8
<212> TYPE: PRT
<213> ORGANISM: Saccharomyces cerevisiae

<400> SEQUENCE: 19

Gly Trp Thr Thr Gly Thr Gly Gly
1               5

<210> SEQ ID NO 20
<211> LENGTH: 8
<212> TYPE: PRT
<213> ORGANISM: Saccharomyces cerevisiae
```

```
-continued

<400> SEQUENCE: 20

Thr Gly Thr Gly Gly Thr Tyr Gly
1               5

<210> SEQ ID NO 21
<211> LENGTH: 5
<212> TYPE: PRT
<213> ORGANISM: Saccharomyces cerevisiae

<400> SEQUENCE: 21

Thr Gly Thr Gly Gly
1               5

<210> SEQ ID NO 22
<211> LENGTH: 5
<212> TYPE: PRT
<213> ORGANISM: Saccharomyces cerevisiae

<400> SEQUENCE: 22

Gly Asp Thr Thr Gly
1               5

<210> SEQ ID NO 23
<211> LENGTH: 8
<212> TYPE: DNA
<213> ORGANISM: Arabidopsis thaliana

<400> SEQUENCE: 23 gwttgtgg                                                                  8

<210> SEQ ID NO 24
<211> LENGTH: 8
<212> TYPE: DNA
<213> ORGANISM: Arabidopsis thaliana

<400> SEQUENCE: 24 tgtggtyg                                                                  8

<210> SEQ ID NO 25
<211> LENGTH: 7
<212> TYPE: DNA
<213> ORGANISM: Arabidopsis thaliana

<400> SEQUENCE: 25 gwgkttg                                                                   7

<210> SEQ ID NO 26
<211> LENGTH: 8
<212> TYPE: DNA
<213> ORGANISM: Arabidopsis thaliana

<400> SEQUENCE: 26 gwttgtgg                                                                  8
```